United States Patent
Reay-Young et al.

(10) Patent No.: US 7,842,042 B2
(45) Date of Patent: Nov. 30, 2010

(54) CONVERGENT TUNNEL GUIDE APPARATUS AND METHOD

(75) Inventors: Clive Reay-Young, Harrogate (GB); Peter Curran, Harrogate (GB)

(73) Assignee: ArthroCare Corporation, Austin, TX (US)

( * ) Notice: Subject to any disclaimer, the term of this patent is extended or adjusted under 35 U.S.C. 154(b) by 254 days.

(21) Appl. No.: 11/131,005

(22) Filed: May 16, 2005

(65) Prior Publication Data

US 2006/0271059 A1    Nov. 30, 2006

(51) Int. Cl.
*A61B 17/60* (2006.01)

(52) U.S. Cl. .................................................... 606/96

(58) Field of Classification Search ............. 606/86–88, 606/95–96, 98, 104; 623/13.11–13.14
See application file for complete search history.

(56) References Cited

U.S. PATENT DOCUMENTS

| | | | |
|---|---|---|---|
| 1,727,590 A | 9/1929 | Thomas | 411/430 |
| 2,778,357 A | 1/1957 | Leibinger et al. | 128/2 |
| 3,896,500 A | 7/1975 | Rambert et al. | 623/13.14 |
| 3,905,356 A | 9/1975 | Fletcher et al. | 600/587 |
| 3,973,277 A | 8/1976 | Semple et al. | 623/13.14 |
| 3,974,621 A | 8/1976 | Stang | 411/75 |
| 4,149,277 A | 4/1979 | Bokros | 623/13.2 |
| 4,187,558 A | 2/1980 | Dahlen et al. | 623/13.14 |
| 4,204,544 A | 5/1980 | Feldstein et al. | 600/375 |
| 4,275,717 A | 6/1981 | Bolesky | 606/63 |
| 4,335,715 A * | 6/1982 | Kirkley | 606/87 |
| 4,347,024 A | 8/1982 | Coldren | 411/11 |
| 4,406,281 A | 9/1983 | Hubbard et al. | 128/846 |
| 4,530,357 A | 7/1985 | Pawloski et al. | 606/180 |
| 4,573,448 A | 3/1986 | Kambin | 606/170 |
| 4,583,554 A | 4/1986 | Mittelman et al. | 600/587 |
| 4,600,005 A | 7/1986 | Hendel | 128/304 |
| 4,600,007 A | 7/1986 | Lahodny et al. | 606/174 |
| 4,708,132 A | 11/1987 | Silvestrini | 606/66 |
| 4,712,542 A | 12/1987 | Daniel et al. | 606/96 |
| 4,776,851 A | 10/1988 | Bruchman et al. | 623/13.11 |

(Continued)

FOREIGN PATENT DOCUMENTS

DE                 9002844           1/1991

(Continued)

OTHER PUBLICATIONS

F.H. Fuh, et al., Anatomic ACL Double-Bundle Reconstruction, Orthopedic Technology Review vol. 7 No. 4, 6 pgs, May/Jun. 2005.

(Continued)

*Primary Examiner*—Thomas C Barrett
*Assistant Examiner*—Michael J Araj
(74) *Attorney, Agent, or Firm*—Matthew Scheele; Brian Szymczak

(57) ABSTRACT

A tunnel guide apparatus and method for forming two convergent tunnels in a bone. The apparatus includes a first bullet member for aiming a guide pin to form a first tunnel in the bone. A second bullet member adjustably connects to the first bullet member, for aiming a guide pin to form a second tunnel in the bone such that the first and second tunnels are convergent. The two bullet members are joined by a guide arm member disposed on a guide arc member such that the first and second bullet members and the guide arm member are adjustable on the guide arc member to form the two tunnels.

24 Claims, 5 Drawing Sheets

U.S. PATENT DOCUMENTS

| | | | | |
|---|---|---|---|---|
| 4,820,279 A | 4/1989 | Dedo | | 604/290 |
| 4,910,901 A | 3/1990 | Boyar | | 40/607 |
| 4,969,471 A | 11/1990 | Daniel et al. | | 600/587 |
| 4,997,433 A | 3/1991 | Goble et al. | | 606/64 |
| 5,037,422 A | 8/1991 | Hayhurst et al. | | 606/72 |
| 5,037,426 A | 8/1991 | Goble et al. | | 606/96 |
| 5,139,520 A | 8/1992 | Rosenberg | | 606/87 |
| 5,147,361 A | 9/1992 | Ojima et al. | | 606/61 |
| D330,591 S | 10/1992 | Rosenberg et al. | | D24/147 |
| 5,152,790 A | 10/1992 | Rosenberg et al. | | 623/13.14 |
| 5,170,800 A | 12/1992 | Smith et al. | | 600/564 |
| 5,176,682 A | 1/1993 | Chow | | 606/72 |
| 5,176,699 A | 1/1993 | Markham | | 606/206 |
| 5,228,448 A | 7/1993 | Byrd | | 600/490 |
| 5,251,646 A | 10/1993 | Bowen | | 128/878 |
| 5,254,129 A | 10/1993 | Alexander | | 606/170 |
| 5,258,003 A | 11/1993 | Ciaglia et al. | | 606/185 |
| 5,266,075 A | 11/1993 | Clark et al. | | 606/138 |
| 5,303,472 A | 4/1994 | Mbanugo | | 30/124 |
| 5,306,301 A | 4/1994 | Graf et al. | | 623/13 |
| 5,314,429 A * | 5/1994 | Goble | | 606/96 |
| 5,324,308 A | 6/1994 | Pierce | | 606/232 |
| 5,330,468 A * | 7/1994 | Burkhart | | 606/96 |
| 5,350,380 A | 9/1994 | Goble et al. | | 606/80 |
| 5,350,383 A * | 9/1994 | Schmieding et al. | | 606/96 |
| 5,364,400 A | 11/1994 | Rego, Jr. et al. | | 606/72 |
| 5,383,471 A | 1/1995 | Funnell | | 600/564 |
| 5,391,169 A | 2/1995 | McGuire | | 606/79 |
| 5,393,302 A | 2/1995 | Clark et al. | | 606/72 |
| RE34,871 E | 3/1995 | McGuire et al. | | 606/73 |
| 5,395,375 A | 3/1995 | Turkel et al. | | 606/83 |
| 5,405,359 A | 4/1995 | Pierce | | 606/232 |
| 5,408,359 A | 4/1995 | Ferrett et al. | | 359/601 |
| 5,423,860 A | 6/1995 | Lizardi et al. | | 606/232 |
| 5,472,452 A | 12/1995 | Trott | | 606/232 |
| 5,475,553 A | 12/1995 | Saliba | | 360/122 |
| 5,489,292 A | 2/1996 | Tovey et al. | | 606/207 |
| 5,529,424 A | 6/1996 | Neubert et al. | | 403/298 |
| 5,556,411 A | 9/1996 | Taoda et al. | | 606/185 |
| 5,562,664 A * | 10/1996 | Durlacher et al. | | 606/96 |
| 5,591,190 A | 1/1997 | Yoon | | 606/185 |
| 5,601,562 A | 2/1997 | Wolf et al. | | 606/86 |
| 5,609,634 A | 3/1997 | Voydeville | | 623/13.11 |
| 5,618,314 A | 4/1997 | Harwin et al. | | 606/232 |
| 5,620,001 A | 4/1997 | Byrd et al. | | 606/202 |
| 5,626,609 A | 5/1997 | Zvenyatsky et al. | | 606/208 |
| 5,632,748 A | 5/1997 | Beck et al. | | 606/89 |
| 5,643,266 A | 7/1997 | Li | | 606/72 |
| 5,643,273 A * | 7/1997 | Clark | | 606/96 |
| 5,645,588 A | 7/1997 | Graf et al. | | 606/151 |
| 5,647,874 A | 7/1997 | Hayhurst | | 606/72 |
| 5,651,368 A | 7/1997 | Napolitano et al. | | 600/490 |
| 5,674,224 A | 10/1997 | Howell et al. | | 606/88 |
| 5,683,359 A | 11/1997 | Farkas et al. | | 604/22 |
| 5,683,471 A | 11/1997 | Incavo et al. | | 128/898 |
| 5,707,395 A | 1/1998 | Li | | 606/232 |
| 5,713,897 A | 2/1998 | Goble et al. | | 606/53 |
| 5,725,541 A | 3/1998 | Anspach et al. | | 606/151 |
| 5,735,867 A | 4/1998 | Golser et al. | | 606/185 |
| 5,769,894 A | 6/1998 | Ferragamo | | 606/148 |
| 5,782,749 A | 7/1998 | Riza | | 600/117 |
| 5,788,701 A | 8/1998 | McCue | | 606/88 |
| 5,791,350 A | 8/1998 | Morton | | 600/590 |
| 5,797,963 A | 8/1998 | McDevitt | | 606/232 |
| 5,813,808 A | 9/1998 | Wu | | 411/32 |
| 5,840,078 A | 11/1998 | Yerys | | 606/151 |
| 5,891,150 A * | 4/1999 | Chan | | 606/96 |
| 5,891,168 A | 4/1999 | Thai | | 606/232 |
| 5,895,425 A | 4/1999 | Grafton et al. | | 606/73 |
| 5,911,695 A | 6/1999 | Watkins et al. | | 600/553 |
| 5,913,860 A | 6/1999 | Scholl | | 606/100 |
| 5,918,604 A | 7/1999 | Whelan | | 128/898 |
| 5,935,129 A | 8/1999 | McDevitt et al. | | 606/72 |
| 5,984,966 A | 11/1999 | Kiema et al. | | 623/13.14 |
| 5,989,253 A | 11/1999 | Bigliardi | | 606/72 |
| 6,015,412 A | 1/2000 | Mifsud | | 606/83 |
| 6,068,648 A | 5/2000 | Cole et al. | | 606/232 |
| D426,305 S | 6/2000 | Hein | | D24/147 |
| 6,080,154 A | 6/2000 | Reay-Young et al. | | 606/60 |
| 6,086,591 A | 7/2000 | Bojarski | | 606/64 |
| 6,099,568 A | 8/2000 | Simonian et al. | | 623/13.11 |
| 6,110,207 A | 8/2000 | Eichhorn et al. | | 623/13.14 |
| 6,117,161 A | 9/2000 | Li et al. | | 606/232 |
| 6,132,433 A | 10/2000 | Whelan | | 606/72 |
| 6,146,406 A | 11/2000 | Shluzas et al. | | 606/232 |
| 6,146,407 A | 11/2000 | Krebs | | 606/232 |
| 6,152,928 A | 11/2000 | Wenstrom | | 606/72 |
| 6,156,039 A | 12/2000 | Thai | | 606/72 |
| 6,187,011 B1 * | 2/2001 | Torrie | | 606/96 |
| 6,214,007 B1 | 4/2001 | Anderson | | 606/73 |
| 6,221,107 B1 | 4/2001 | Steiner et al. | | 623/13.14 |
| 6,254,606 B1 * | 7/2001 | Carney et al. | | 606/102 |
| 6,306,138 B1 | 10/2001 | Clark et al. | | 606/65 |
| 6,319,270 B1 | 11/2001 | Grafton et al. | | 606/232 |
| 6,328,758 B1 | 12/2001 | Tornier et al. | | 606/232 |
| 6,355,053 B1 | 3/2002 | Li | | 606/232 |
| 6,355,066 B1 | 3/2002 | Kim | | 623/13.14 |
| 6,371,124 B1 | 4/2002 | Whelan | | 128/898 |
| 6,379,361 B1 | 4/2002 | Beck, Jr. et al. | | 606/72 |
| 6,402,757 B1 | 6/2002 | Moore, III et al. | | 606/80 |
| 6,440,134 B1 | 8/2002 | Zaccherotti et al. | | 606/62 |
| 6,478,753 B2 | 11/2002 | Reay-Young | | 600/595 |
| 6,491,714 B1 | 12/2002 | Bennett | | 606/232 |
| 6,499,486 B1 | 12/2002 | Chervitz et al. | | 128/898 |
| 6,517,578 B2 | 2/2003 | Hein | | 623/13.13 |
| 6,527,795 B1 | 3/2003 | Lizardi | | 606/232 |
| 6,533,816 B2 | 3/2003 | Sklar | | 623/13.14 |
| 6,544,273 B1 | 4/2003 | Harari et al. | | 606/151 |
| 6,547,800 B2 | 4/2003 | Foerster et al. | | 606/151 |
| 6,551,343 B1 | 4/2003 | Tormala et al. | | 606/213 |
| 6,562,071 B2 | 5/2003 | Jarvinen | | 623/13.14 |
| 6,610,064 B1 | 8/2003 | Goble et al. | | 606/72 |
| 6,610,080 B2 | 8/2003 | Morgan | | 606/232 |
| 6,623,524 B2 | 9/2003 | Schmieding | | 623/13.14 |
| 6,635,074 B2 | 10/2003 | Bartlett | | 606/232 |
| 6,652,533 B2 | 11/2003 | O'Neil | | 606/100 |
| 6,652,560 B1 | 11/2003 | Gerke et al. | | 606/232 |
| 6,736,847 B2 | 5/2004 | Seyr et al. | | 623/13.14 |
| 6,780,188 B2 | 8/2004 | Clark et al. | | 606/73 |
| 6,802,862 B1 | 10/2004 | Roger et al. | | 623/13.14 |
| 6,808,528 B2 | 10/2004 | Justin | | 606/72 |
| 6,878,166 B2 | 4/2005 | Clark et al. | | 623/13.12 |
| 6,905,513 B1 | 6/2005 | Metzger | | 623/20.17 |
| 6,991,631 B2 | 1/2006 | Woloszko et al. | | 606/41 |
| 6,994,725 B1 | 2/2006 | Goble | | 623/13.14 |
| 7,175,632 B2 | 2/2007 | Singhatat et al. | | 606/72 |
| 7,226,469 B2 | 6/2007 | Benavitz et al. | | 606/232 |
| D547,451 S | 7/2007 | Asfora | | D24/146 |
| 2003/0088874 A1 | 5/2003 | Cavazzoni | | 623/13.11 |
| 2004/0193167 A1 | 9/2004 | Tucciarone et al. | | 606/73 |
| 2005/0192582 A1 | 9/2005 | Reay-Young | | 606/79 |
| 2005/0222619 A1 | 10/2005 | Dreyfuss et al. | | 606/72 |
| 2006/0178673 A1 | 8/2006 | Curran | | 606/100 |
| 2006/0235516 A1 | 10/2006 | Cavazzoni | | 623/13.14 |
| 2006/0253119 A1 | 11/2006 | Berberich et al. | | 606/72 |
| 2006/0276841 A1 | 12/2006 | Barbieri et al. | | 606/232 |
| 2007/0021751 A1 | 1/2007 | Reay-Young et al. | | 606/72 |
| 2007/0213730 A1 | 9/2007 | Martinek et al. | | 606/72 |
| 2007/0260249 A1 | 11/2007 | Boyajian et al. | | 606/72 |

FOREIGN PATENT DOCUMENTS

| | | |
|---|---|---|
| DE | 29607352 | 9/1996 |
| EP | 238223 | 9/1987 |

| | | |
|---|---|---|
| EP | 279129 | 8/1988 |
| EP | 317406 | 5/1989 |
| EP | 379789 | 11/1989 |
| EP | 346469 | 12/1989 |
| EP | 574707 | 12/1993 |
| EP | 619982 | 3/1994 |
| EP | 0 674 880 | 3/1995 |
| EP | 706780 | 4/1996 |
| EP | 0865774 | 9/1998 |
| EP | 1066805 | 6/2000 |
| EP | 1180351 | 2/2002 |
| FR | 2395012 | 1/1979 |
| FR | 2590792 | 6/1987 |
| FR | 2683715 | 5/1993 |
| FR | 2725615 | 4/1996 |
| FR | 2732211 | 4/1996 |
| GB | 2288739 | 11/1995 |
| GB | 2337463 | 11/1999 |
| SU | 1521465 | 11/1989 |
| WO | 93/25148 | 12/1993 |
| WO | 95/11631 | 5/1995 |
| WO | 96/03926 | 2/1996 |
| WO | 96/29029 | 9/1996 |
| WO | 96/39934 | 12/1996 |
| WO | 97/19634 | 6/1997 |
| WO | 97/20522 | 6/1997 |
| WO | 98/12991 | 4/1998 |
| WO | 98/12992 | 4/1998 |
| WO | 98/22048 | 5/1998 |
| WO | 98/38937 | 9/1998 |
| WO | 99/52472 | 10/1999 |
| WO | 99/59488 | 11/1999 |
| WO | 03/088874 | 10/2003 |

OTHER PUBLICATIONS

ArthroCare SportsMedicine Product Catalogue, 3.1 Knee (p. 44 p. 52), 4 pgs, Jul. 2005.
PCT Notification of the International Search Report and Written Opninon for PCT/US06/19100, 7 pgs Mailed Sep. 27, 2007.
PCT Notification of the International Search Report and Written Opninon for PCT/US05/17382, 11 pgs, Mailed Oct. 23, 2007.
PCT Notification of the International Search Report and Written Opninon for PCT/US05/01629, 6 pgs, Mailed Apr. 22, 2008.
Smith & Nephew, "Arthroscopic Repair of a Bankart Lesion Using TAG Suture Anchors," 12 pgs May 1996.
UK Search Report for GB 9915550 1 pg, Jun. 13, 2000.
UK Search Report for GB 9929599 1 pg, Oct. 12, 2000.
UK Search Report for GB 0116605 1 pg, Mar. 27, 2002.
UK Search Report for GB 0013037 1 pg, Mar. 20, 2001.
UK Search Report for GB 0208667 1 pg, Feb. 24, 2003.
European Search Report for EP 00113471 2 pgs, Jan. 26, 2001.
European Search Report for EP 00311077 2 pgs, Mar. 6, 2001.
European Search Report for EP 00830524 2 pgs, Aug. 8, 2001.
European Search Report for EP 01112516 2 pgs, Aug. 7, 2003.
European Search Report for EP 02013879 4 pgs, May 25, 2004.
European Search Report for EP 02014485 2 pgs, Nov. 4, 2003.
European Search Report for EP 97122626 2 pgs, Apr. 21, 1998.
European Search Report for EP 98301702 2 pgs, Jun. 23, 1998.
European Search Report for EP 99302529 2 pgs, Jul. 8, 1999.
PCT International Search Report for PCT/GB03/01606 3 pgs, Mailed Sep. 4, 2003.
PCT International Search Report for PCT/US06/04674 1 pg, Mailed Jul. 25, 2007.
PCT Written Opinion for PCT/US06/04674 4 pgs, Mailed Jul. 25, 2007.

* cited by examiner

CONVERGENT TUNNEL GUIDE APPARATUS AND METHOD

BACKGROUND

1. Field of the Invention

This invention relates to a tunnel guide apparatus, in particular a tunnel guide apparatus comprising two bullet members adapted to form two convergent tunnels in a bone, and methods thereof.

2. Description of the Prior Art

In arthroscopy, a common procedure is to replace a damaged ligament with an implant. For example, with reference to FIGS. 1-3, to replace a damaged anterior cruciate ligament (ACL) (11) or a damaged posterior cruciate ligament (PCL) (12) in the knee joint (10), the damaged ligament is removed and the surfaces of the joint cleaned. Thereafter, two tunnels (13, 14) are formed to receive the implant between the condyle of the tibia (15) and condyle of the femur (16).

To form the tunnels (13, 14), a single-tunnel apparatus (18) shown schematically in FIG. 3 may be used. In using this single-tunnel apparatus, the distal tip of a cannulated bullet (19) is pressed against the tibia (15) to determine the direction of the tunnel in the bone. Once the direction is determined, the bullet is locked in place and a guide pin is driven into the bone (15) through a cannula in the bullet (19). Thereafter, the bullet is removed and a drill is threaded on the guide pin to form the tunnel. The implant is inserted in the tunnels (13, 14) between the femur and the tibia, and secured with an internal screw or another mechanism as is known in the art. Similarly, a screw is used to secure the implant in the condyle of the tibia. A method of securing an implant using single tunnels is described in co-pending U.S. patent application Ser. No. 10/822,101, filed Apr. 8, 2004, herein incorporated by reference.

In procedures to replace ACL and PCL ligaments using single tunnels, and with reference to FIG. 3 since the implant is placed in a tunnel (13, 14), the implant assumes the shape of the tunnel, i.e., it is cylindrical. A cylindrical shape having a uniform cross-section however is not the shape of the natural ligament and may be insufficient in controlling the rotational stability of the knee joint.

In a review of single-tunnel/single-bundle ACL reconstructions cited in "Anatomic Double-Bundle ACL Reconstruction: The Restoration of Normal Kinematics", Dr. F. H. Fu et al. (2005), herein incorporated by reference, patients reported residual instability and pain following single-bundle reconstruction. On the other hand, there are indications that ACL double-bundle reconstruction results in a closer restoration of normal knee kinematics and provides better rotational stability of the knee joint.

Based on these considerations it has been hypothesized that double-bundle ACL reconstruction provides superior restoration of the knee stability and functional outcomes compared to a single-bundle ACL reconstruction. Accordingly, in view of these considerations it is an objective to provide for an apparatus and method to efficiently perform ACL and PCL double-bundle reconstruction.

SUMMARY OF THE INVENTION

In one embodiment, the present apparatus comprises a tunnel guide for forming two converging tunnels in a bone, comprising a first bullet member adapted to aim a guide pin through the bone to form the path of the first tunnel; and a second bullet member adapted to aim a guide pin through the bone to form the path of the second tunnel in the bone, wherein the second bullet member is adjustably connected to the first bullet member, and wherein the first and second bullet members are positioned such that the first and second tunnels are convergent.

In another embodiment, the apparatus comprises a tunnel guide for forming tunnels in a bone, comprising: a first bullet member adapted to aim a guide pin through the bone along a first path to form a first tunnel; a second bullet member adapted to aim a guide pin through the bone along a second path to form a second tunnel, the second bullet member adjustably connected to the first bullet member, and wherein the first and second bullet members are positioned such that the first and second tunnels are convergent; and a guide arm member disposed on a distal portion of the guide arc member, wherein the first and second bullet members and the guide arm member are adjustable on the guide arc member to form the first and second tunnels in the bone.

In another embodiment, the method comprises: securing a tunnel guide apparatus onto the bone, the tunnel guide apparatus comprising: a first bullet member adapted to aim a first guide pin through the bone along a first path to form a first tunnel in the bone, and a second bullet member adapted to aim a second guide pin through the bone along a second path to form a second tunnel in the bone, the second bullet member adjustably connected to the first bullet member, wherein the first and second bullet members are positioned such that the first and second tunnels are convergent; inserting the first guide pin through the first bullet member to form the first tunnel; and inserting the second guide pin through the second bullet member to form the second tunnel.

Advantageously, since the present invention allows for formation of two converging tunnels in the bone, the present invention allows for efficient double-bundle reconstruction of ligament. In particular, the present apparatus can be used to replicate the normal ACL in having an antero medial bundle and a postero lateral bundle as described herein.

DETAILED DESCRIPTION OF A PREFERRED EMBODIMENT

Figure 1:
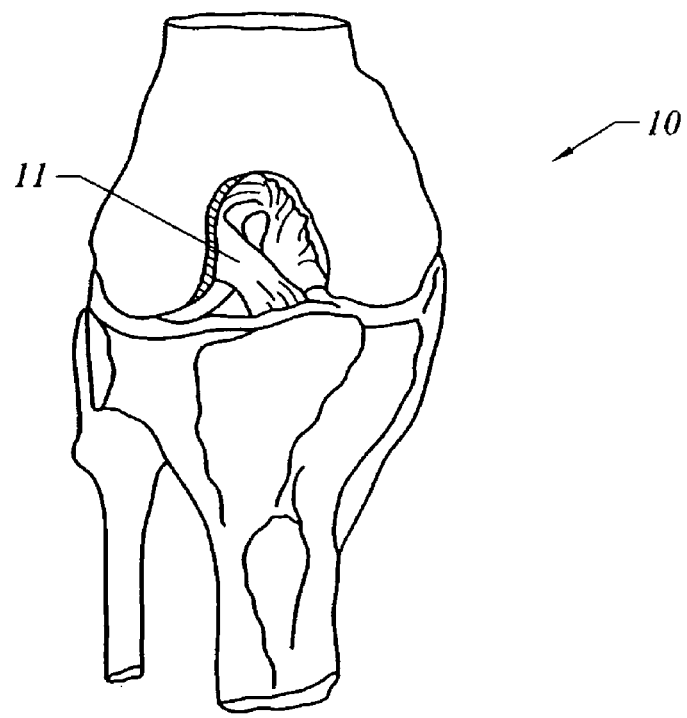
FIG. 1 is an anterior view of a knee joint to illustrate the location of the ACL wherein embodiments of the present invention are useable.
Figure 2:
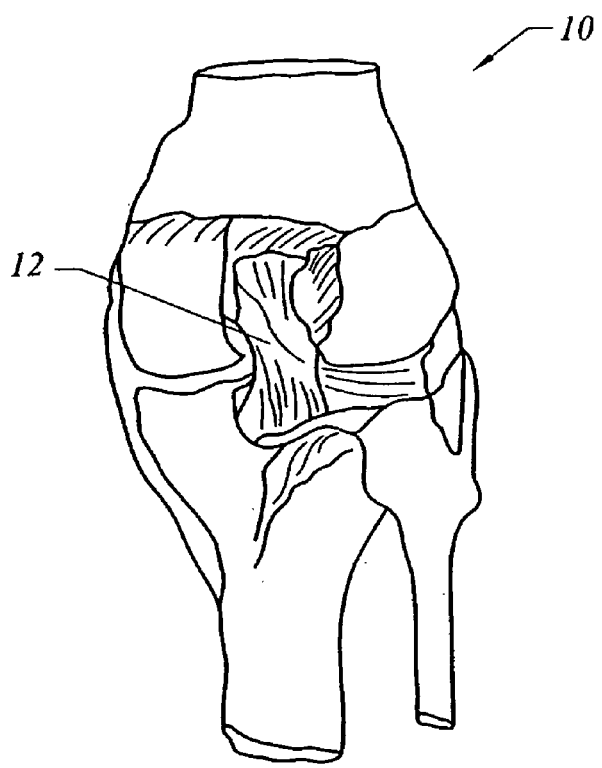
FIG. 2 is a posterior view of a knee joint to illustrate the location of the PCL wherein embodiments of the present invention are useable.
Figure 3:
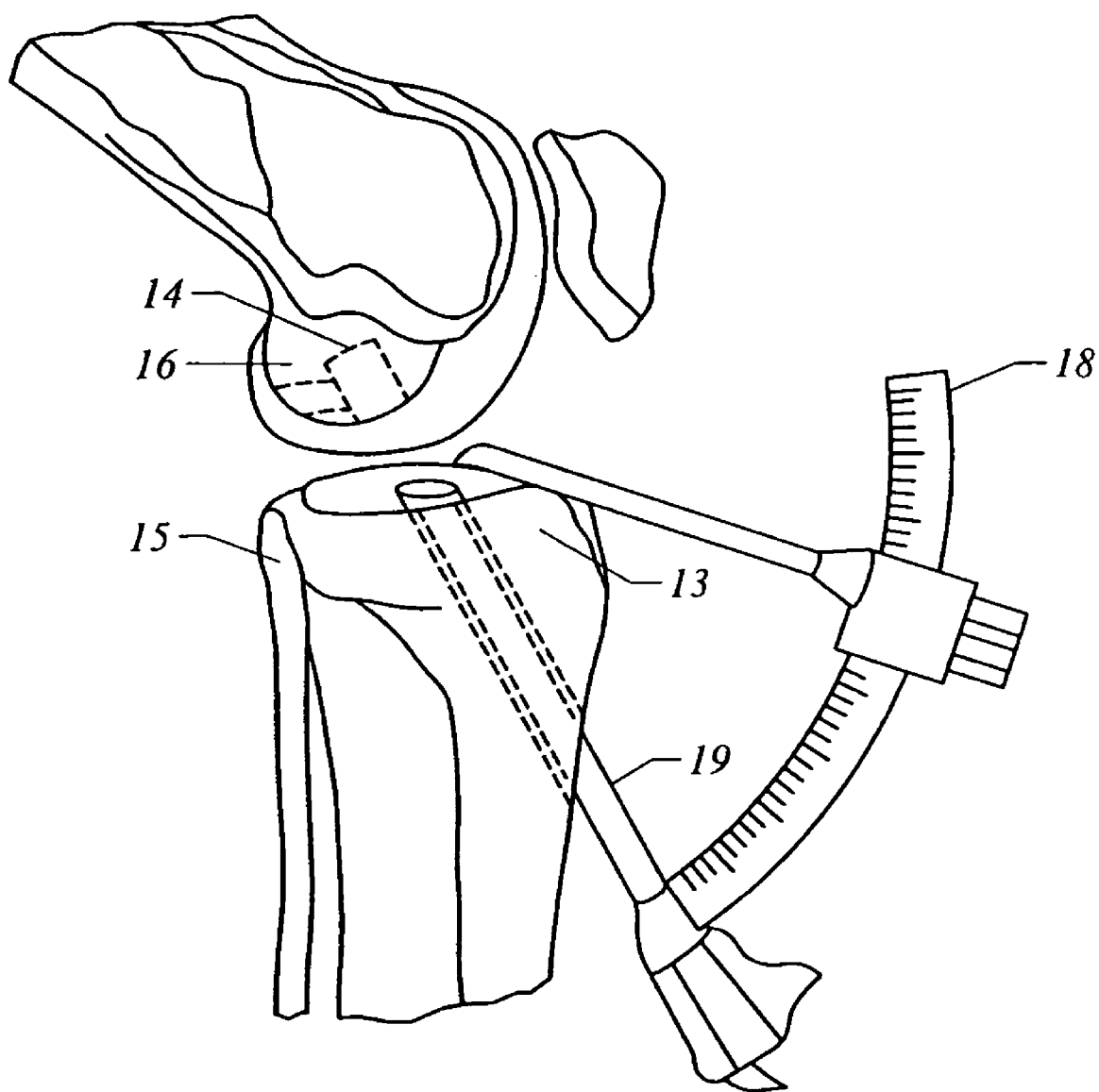
FIG. 3 is an illustration of the conventional apparatus used in ACL and PCL reconstruction single-bundle, single tunnel procedures.
Figure 4:
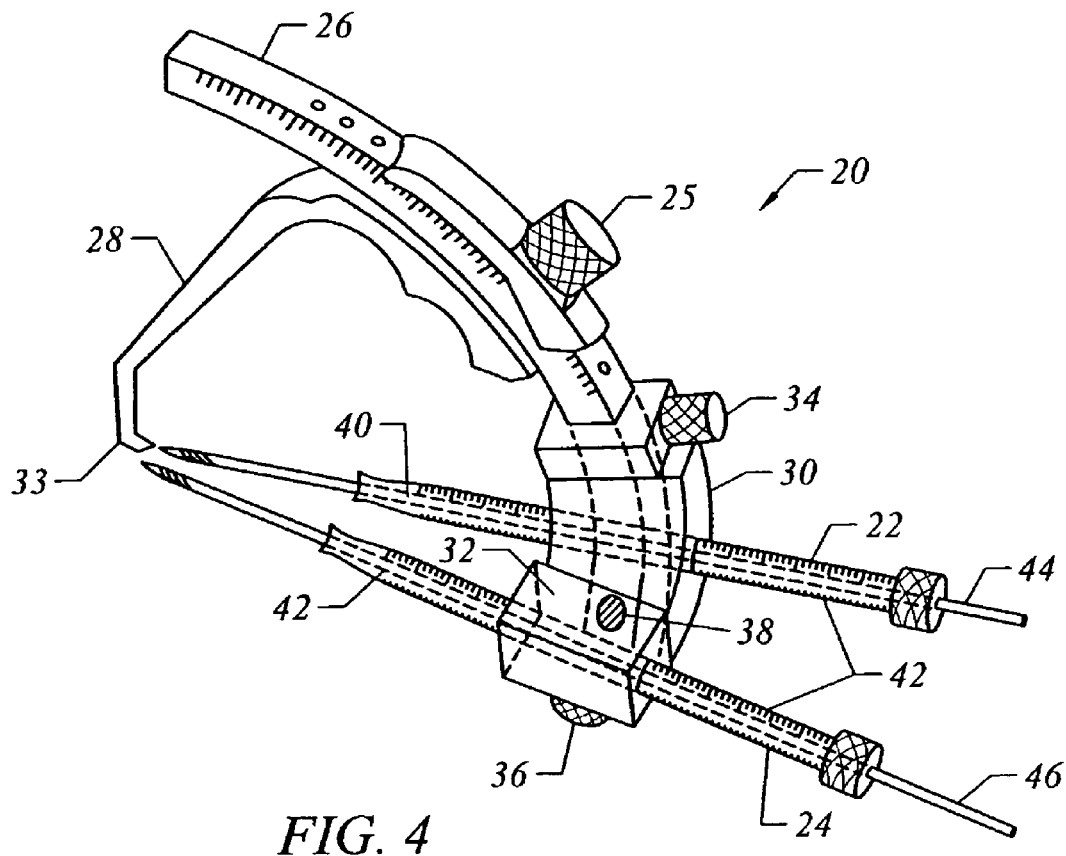
FIG. 4 is a perspective view of an embodiment of the present invention comprising double bullet members for forming convergent double tunnels.
Figure 5:
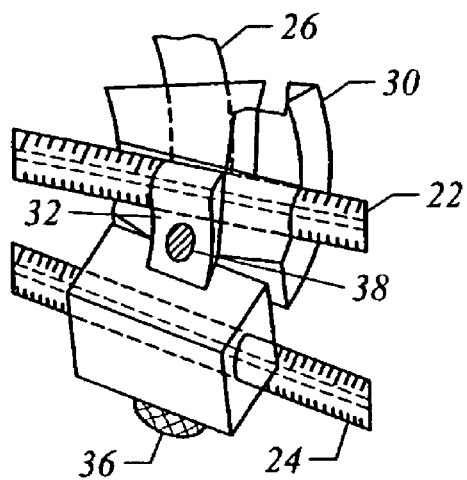
FIG. 5 is a perspective view of an embodiment of the present invention showing first and second bullet members separated by an outrigger portion for forming convergent double tunnels.
Figure 6:
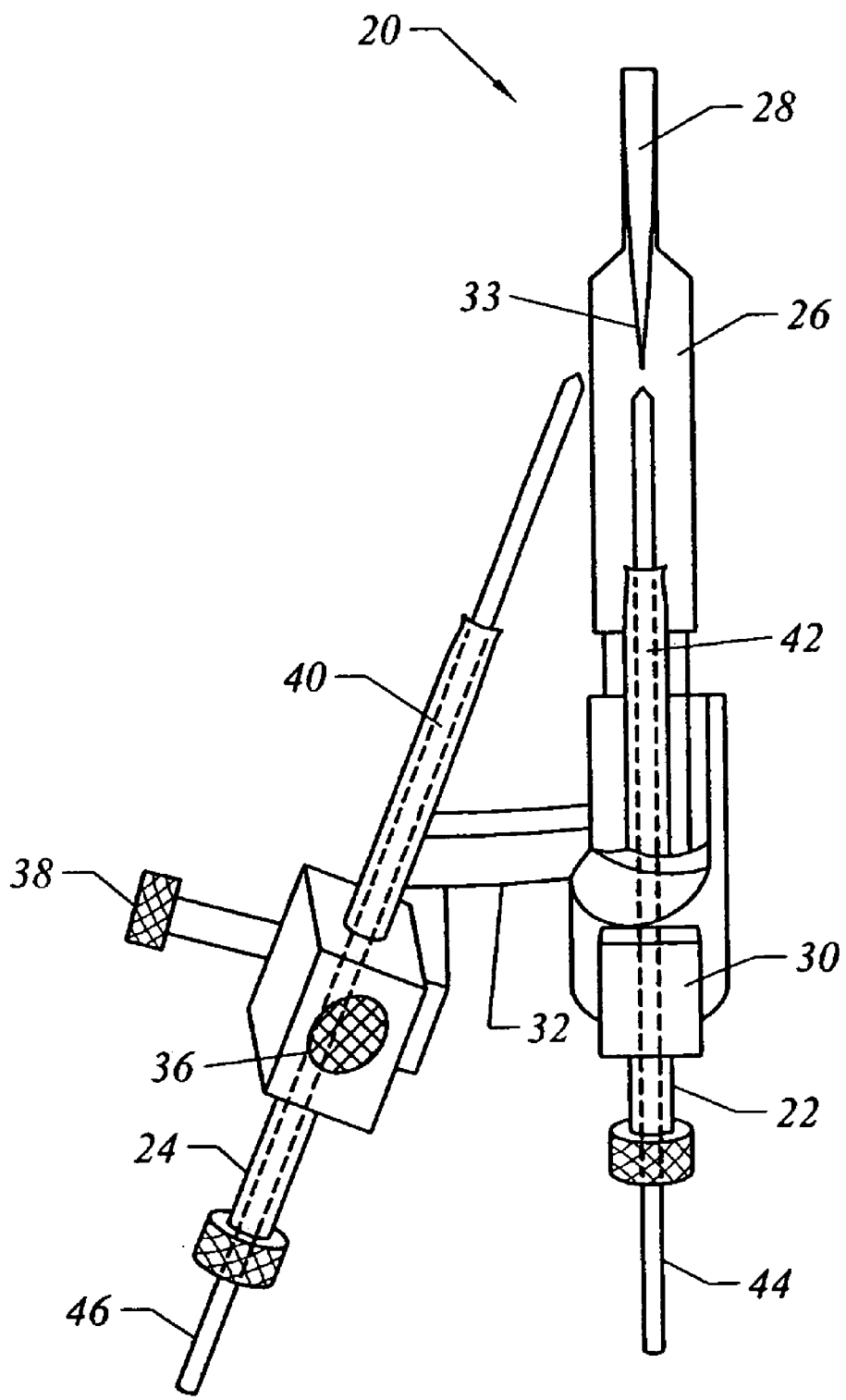
FIG. 6 is an alternative perspective view of an embodiment of the invention comprising bullet members for forming convergent double tunnels.

Embodiments of the present invention, illustrated in FIGS. 4-7 and described herein, provide for an apparatus and method for forming convergent double-bundle tunnels in reconstructive ligament surgery. In the various embodiments described herein, a procedure for double-bundle ACL reconstructive surgery in a knee joint is used to illustrate the invention. However it will be appreciated by those ordinarily skilled in the art that since the present invention is readily adapted for similar procedures involving ligament replacement, therefore the invention is not limited to the embodiments described but encompasses apparatus and methods wherein convergent tunnels are formed as described and claimed herein.

The invention in an embodiment as illustrated in the perspective views of FIGS. 4-7 comprise a tunnel guide including: first and second bullet members (22, 24) disposed on a proximal portion of a guide arc member (26); and guide arm member (28) disposed on a distal portion of guide arc (26) member, wherein first and second bullet members (22,24) and guide arm member (28) are adjustable on the guide arc member (26) for forming a first and a second tunnels (50, 52) in the bone, wherein the first and second tunnels are convergent in the bone.

Figure 7:
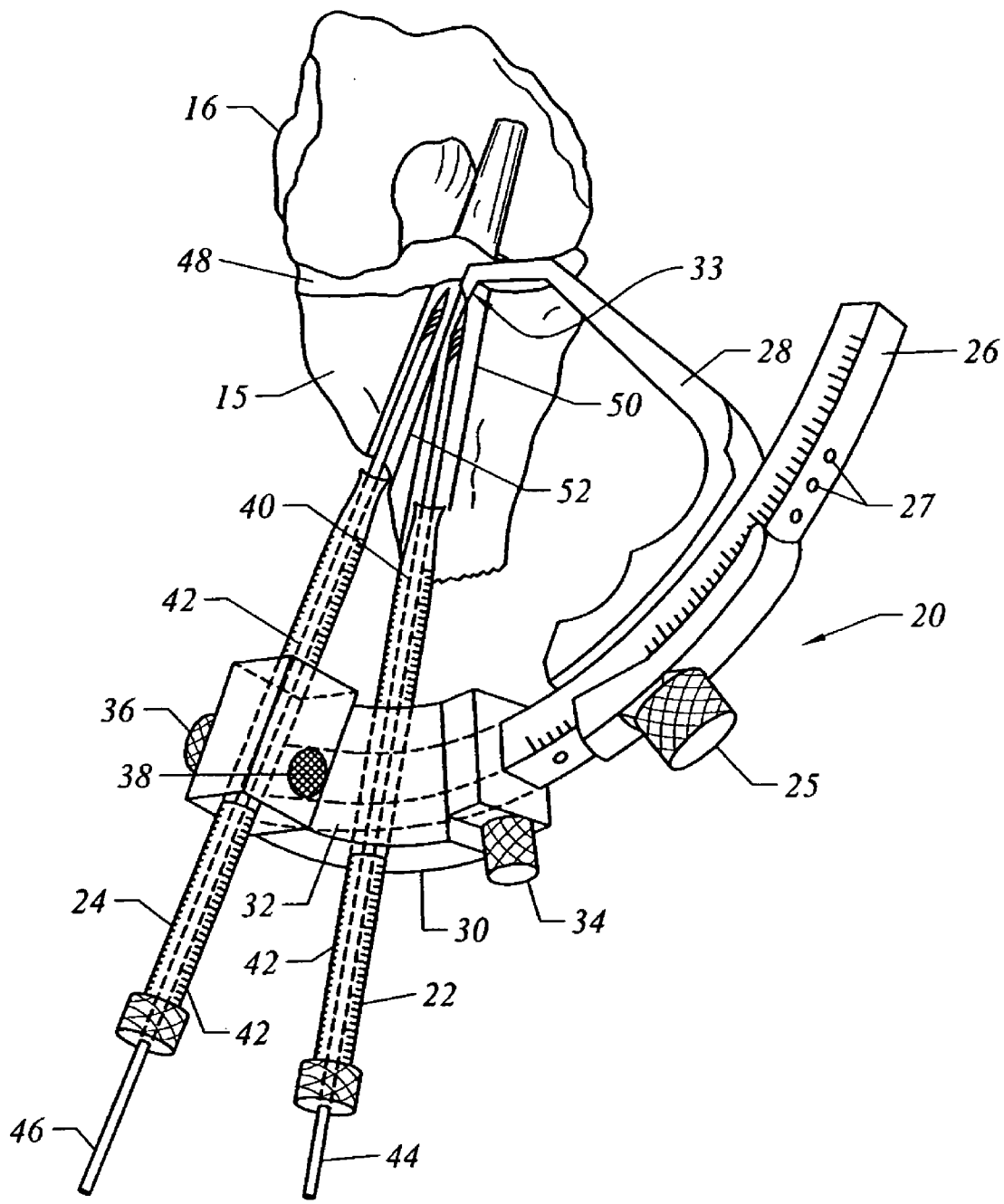
FIG. 7 is a perspective view of an embodiment of the present invention wherein the apparatus is used to form double convergent tunnels.

With reference to FIG. 7, the guide arc member (26) in one embodiment comprises a curved shaft having a generally frusta-conical cross-section and adapted to allow for insertion of the distal tip (33) of the guide arm (28) in a space (48) between the tibia (15) and the femur (16) in the knee joint. With the tip (33) hooked in the space as shown in FIG. 7, the guide arm apparatus (20) is further stabilized against the knee by advancing bullet members (22, 24) against the tibia bone (15). The guide arm (28) is slidably adjusted on the guide arc (26) by slackening or tightening adjusting a first screw member (25) in dimples (27) on the guide arm, first bullet member (22) is slidably attached on the distal end of guide arm member (28) and lockable in position relative to the bone (15) by a clip (30). Similarly, the second bullet member (24) is slidably attached to the distal end of the guide arm member (28) through an outrigger member (32). The second bullet member is removably attached to the outrigger member by a second screw member (36).

In a preferred embodiment, as shown in FIGS. 4-7, the lateral position of the second bullet member (24) is fixed relative to the first bullet member (22) by a rigid outrigger member (32) which is slidably attached to guide arm member (28). In this embodiment, the outrigger (32) is slidably adjustable on guide arc (26) by slackening or tightening a third screw member (34) in dimples (27) on the guide arc (26). In one embodiment, the second bullet member (24) is rotatable relative to the rigid outrigger member (32) about an axis defined by fourth screw member (38), for placement against the tibia (15).

In one embodiment, first bullet member (22) and second bullet member (24) are generally cylindrical tubes with cannulated cores (40, 42) adapted for aiming of guide pins (44, 46) through the bone to form first and second tunnels (50, 52) in the tibia (15). In a preferred embodiment, first bullet members (22) are slidably adjustable relative to the tibia (15) by manipulating clip 30; similarly, second bullet member (24) is adjustable relative to the tibia (15) by slackening or tightening third screw member (36). Preferably, bullet first and second members (22, 24) are calibrated with marks (42) to locate positions of bullet members (22, 24) relative to the tibia (15).

In a preferred embodiment, the first (22) and second (24) bullet members are adjustable to form the first and second tunnel (50, 52) on the proximal surface of the bone (15) at about 7 mm center-to-center apart. The center-to-center distance is distance between the radial centers of the tunnels. Similarly, in one embodiment, first (22) and second (24) bullet members are adjustable for forming the first (44) and second (46) tunnels on the distal portion of the bone (15) at about 2 mm center-to-center apart. The center-to-center distance between the tunnels is determined by the length of the outrigger member (32), and therefore by adjusting this length, alternative center-to-center distances can be obtained.

In another embodiment, the present invention comprises a method of forming convergent double tunnels in bone at a target location, using the apparatus. This method, which involves a series of steps, includes a first step of attaching a tunnel guide apparatus onto said bone. This can be done by hooking the distal tip (33) of the guide arm in a space (48) between the bones and adjusting the position of the bullet members (22, 24) on the bone to stabilize the apparatus. Next, guide pins (44, 46) are inserted in the cannulas (40, 42) of the bullet members (22, 24) and into the to bone to mark the location of the longitudinal axis of the tunnels in the bone. Thereafter, the apparatus is removed leaving the guide pins in the bone.

Next, a cannulated drill bit is threaded on the guide pin to form each tunnel. In this embodiment of the method, once the guide tip is inserted in a space within the joint, the position of first and second bullet members (22, 24) on the bone can be adjusted by slackening and or tightening first, second, third and fourth screw members (25, 34, 36 and 38). Thus for ALC and PCL repairs, the guide always provides centers at a fixed lateral distance apart. Further, the rotational element on the outrigger allows for adjustment of the position of the second tunnel in AP relative to the first tunnel more commonly posterior to the first. Thus, the present guide can be used to replicate the normal ACL in having an antero medial bundle and a postero lateral bundle. As such the distal tip guide is placed in the position that the surgeon desires as the centre of the antero medial bundle, and the outrigger determines the position of the postero lateral bundle in relation to this. The rotational element allows the surgeon to adjust the posterior element of the postero lateral bundle in relation to the antero medial.

Among the advantages of providing two or more bone tunnels in the tibia to support ligament bundle is that this surgical reconstruction more closely resembles the knee natural anatomy as compared to a reconstruction using only a single, uniform cross-section tunnel formed in the tibial condyle.

While the invention is described in the context of an apparatus and method for ACL and PCL reconstructive procedures, one ordinarily skilled in the art will appreciate that the invention can be practiced with obvious modifications in other double-bundle procedures, for example, in the rotator cuff. Thus the scope of the invention therefore is not limited to the embodiments described herein, but is limited only by the scope of the appended claims and their legal equivalents.

What is claimed is:

1. A tunnel guide apparatus for forming convergent tunnels in a bone, comprising:

a first tubular bullet member comprising a lumen, the first bullet member disposed in a first plane and slidably adjustable toward and away from said bone in order to contact said bone and operable to aim a first guide pin through said bone along a first path to form a first tunnel in said bone;

an outrigger member slidably disposed on a guide arc member, the outrigger member movable on the guide arc member in an arcuate path relative to the first tubular bullet member, the arcuate path disposed in the first plane; and a second tubular bullet member comprising a lumen, the
second bullet member slidably adjustable toward and
away from said bone in order to contact said bone and
operable to aim a second guide pin through said bone
along a second path to form a second tunnel in said bone,
the second tubular bullet member removably and slidably attached to the outrigger member wherein the second tubular bullet member is laterally spaced away from
the first tubular bullet member, wherein said first and second bullet members are positioned such that said first and second tunnels are convergent.

2. The tunnel guide apparatus of claim 1, wherein each of said first and second bullet members comprises a rigid tube through which said first and second guide pins are respectively insertable to form said tunnels.

3. The tunnel guide apparatus of claim 2, wherein said rigid tube of said first guide member comprises a first lumen for determining the direction of said first tunnel, and wherein said rigid tube of said second guide member comprises a second lumen for determining the direction of said second tunnel in said bone.

4. The tunnel guide apparatus of claim 3, wherein said first lumen is adapted for passing a first guide pin therethrough, and said second lumen is adapted passing a second guide pin therethrough, to form said first and second tunnels.

5. The tunnel guide apparatus of claim 2, wherein said first and second bullet members comprise calibration marks for determining the position of said first and second bullet members to determine the direction of said first and second tunnels.

6. The tunnel guide apparatus of claim 2, wherein said first and second guide pins are adapted for drilling said first and second tunnels in said bone.

7. The tunnel guide apparatus of claim 1, wherein the guide arc member is operable for orienting said first and second bullet members relative to each another.

8. The tunnel guide apparatus of claim 7, further including a clip member for securing said first bullet member on said guide arc member in forming said first tunnel.

9. The tunnel guide apparatus of claim 7, wherein the outrigger member is operable to slidably attach said second bullet member on said guide arc member in forming said second tunnel.

10. The tunnel guide apparatus of claim 9, further including a locking member for removably attaching said outrigger member onto said guide arc member, and for allowing movement of said second bullet member in a plane parallel to said guide arc member in forming said second tunnel.

11. The tunnel guide apparatus of claim 9, further including a locking screw member for locking said second bullet member relative to said guide arc member in said plane parallel to said guide arc member.

12. The tunnel guide apparatus of claim 7, wherein said guide arc member comprises a curved shaft portion for lockably positioning said first and second bullet members thereon to form said first and second tunnels.

13. The tunnel guide apparatus of claim 1, further including a guide arm member having a tip that is adapted to engage a bone condyle.

14. The tunnel guide apparatus of claim 13, wherein said guide arm member comprises a distal tip portion for aligning said first and second bullet members to form said first and second tunnels.

15. The tunnel guide apparatus of claim 1, wherein said first and second bullet members are adjustable to form said first and second tunnels proximally on said bone at about 7 mm center-to-center apart.

16. The tunnel guide apparatus of claim 1, wherein said first and second bullet members are operable to form said first and second tunnels distally on said bone at about 2 mm center-to-center apart.

17. A tunnel guide apparatus for creating convergent tunnels in a bone at a target location, comprising:

a first tubular bullet member comprising a lumen, the first bullet member disposed in a first plane and slidably adjustable relative to said bone in order to contact said bone and operable to aim a guide pin through said bone along a first path to form a first tunnel in said bone;

an outrigger member slidably disposed on a guide arc member, the outrigger member movable on the guide arc member in an arcuate path relative to the first tubular bullet member, the arcuate path disposed in the first plane;

a second tubular bullet member comprising a lumen, the second bullet member slidably adjustable relative to said bone in order to contact said bone and operable to aim a guide pin through said bone along a second path to form a second tunnel in said bone, the second tubular bullet member removably and slidably attached to the outrigger member wherein the second tubular bullet member is laterally spaced away from the first tubular bullet member, wherein said first and second bullet members are positioned such that said first and second tunnels are convergent; and a guide arm member disposed on a distal portion of the guide arc member, wherein said first and second bullet members and said guide arm member are adjustable on said guide arc member for forming said first and a second tunnels in said bone.

18. The tunnel guide of claim 17, wherein said target location comprises bones in the condyle of the femur and the condyle of the tibia.

19. A method of forming convergent tunnels in a bone at a target location, said method comprising:

attaching a tunnel guide apparatus onto said bone, said tunnel guide apparatus comprising: a first bullet member operable to aim a first guide pin through said bone along a first path to form a first tunnel in said bone, the first tubular bullet member disposed in a first plane;

an outrigger member slidably disposed on a guide arc member, the outrigger member movable on the guide arc member in an arcuate path relative to the first tubular bullet member, the arcuate path disposed in the first plane; and a second bullet member operable to aim a second guide pin through said bone along a second path to form a second tunnel in said bone, the second tubular bullet member removably and slidably attached to the outrigger member wherein the second tubular bullet member is laterally spaced away from the first tubular bullet member, wherein said first and second bullet members are positioned such that said first and second tunnels are convergent; and slidingly adjusting the outrigger member along the guide arc member relative to the first tubular member;

slidingly adjusting said first and second bullet members relative to said bone in order to contact said bone;

inserting said first guide pin through said first bullet member to form said first tunnel; and inserting said second guide pin through said second bullet member to form said second tunnel.

20. The method of claim 19, wherein said target location comprises bones in the condyle of the femur and the condyle of the tibia.

21. The method of claim 19, further comprising removing said guide apparatus and leaving said guide pins in said bone.

22. The method of claim 19, further including rotating said second bullet member in a plane parallel to said guide arc member to form said second tunnel.

23. The method of claim 19, further including using said apparatus to form said first and second tunnels proximally on said bone and spaced apart at about 7 mm center-to-center.

24. The method of claim 19, further including using said tunnel guide apparatus to form said first and second tunnels distally on said bone and spaced apart at about 2 mm center-to-center.

* * * * *